United States Patent [19]
Fuse et al.

[11] Patent Number: 5,662,104
[45] Date of Patent: Sep. 2, 1997

[54] METHOD OF MEASURING THE QUANTITY OF ATTENUATION OF LIGHT TRANSMITTED THROUGH BLOOD AND PHOTO SENSOR USED FOR THE METHOD

[75] Inventors: Masayoshi Fuse; Cheng-tai Xie, both of Tokyo, Japan

[73] Assignee: Nihon Kohden Corporation, Tokyo, Japan

[21] Appl. No.: 419,693

[22] Filed: Apr. 11, 1995

[30] Foreign Application Priority Data

Apr. 11, 1994 [JP] Japan .................................. 6-072033

[51] Int. Cl.⁶ .................................................. A61B 5/00
[52] U.S. Cl. ............................................ 128/633; 128/639
[58] Field of Search .......................... 128/633, 664–667, 128/639; 356/39, 40, 41

[56] References Cited

U.S. PATENT DOCUMENTS 4,301,808 11/1981 Taus .
5,247,931 9/1993 Norwood .................... 128/633
5,413,101 5/1995 Sugiura ........................ 128/633

FOREIGN PATENT DOCUMENTS

3910749 10/1990 Germany .
9115990 10/1991 WIPO .

*Primary Examiner*—Lee S. Cohen
*Assistant Examiner*—Bryan K. Yarnell
*Attorney, Agent, or Firm*—Sughrue, Mion, Zinn, Macpeak & Seas

[57] ABSTRACT

An external auditory canal arm having a photo sensing element at the distal end thereof is inserted into an external auditory meatus. A contact piece 1b having a light emitting element is set to a location near an ear lobe on the surface of a skin of the temporal region of a subject. Light that is emitted from the light emitting element and transmitted through the superficial temporal artery region, is received by the photo sensing element. A variation of the quantity of light when passing through blood flowing through the superficial temporal artery, which is caused by light absorptive materials in the blood, is detected, to thereby obtain oxygen saturation, cardiac output and blood volumes, and the like in the blood.

10 Claims, 13 Drawing Sheets

METHOD OF MEASURING THE QUANTITY OF ATTENUATION OF LIGHT TRANSMITTED THROUGH BLOOD AND PHOTO SENSOR USED FOR THE METHOD

BACKGROUND OF THE INVENTION

1. Field of the Invention

The present invention relates to a transmitted light attenuation measuring method in which a variation of the quantity of light when passing through blood flowing through an artery of a living body, which is caused by light absorptive materials in the blood, is detected and oxygen saturation, cardiac output and blood volumes, and the like in the blood are obtained on the results of the detection, and a photo sensor used for the measurement. More particularly, the invention relates to a blood transmitted light attenuation measuring method for detecting light transmitted through a superficial temporal artery region, and a photo sensor used for the measurement.

2. Related Art

A probe for the photo sensor is known for the probe used in a pulsative wave spectral measuring method for measuring oxygen saturation in blood of a living body and cardiac output and blood volumes by injecting a dye into blood. The known probe is attached to an ear lobe, a concha, or a finger tip of the living body. A light emitting piece as a light emitting means, such as a LED, projects rays of light into the body of the living body. Light transmitted therethrough is received by a photo sensing piece as a photo sensing means, such as a Photo Diode. Light absorptive material in blood flowing through an artery in tissue near to its mounting portion is detected on the basis of the received light.

The attachment of the probe to an ear lobe, a concha, or a finger tip of the living body is easy. When it is attached to the finger tip, a pulsative wave signal of a large amplitude can be obtained. When the motive nerves of the blood vessel are stimulated by a nerve reflection caused by deep breathing or injection liquid, the blood flow varies, so that the measurement is instable.

When the probe is attached to the ear, the measurement is little affected by the vessel contraction owing to the nerve reflection, but the amplitude of the pulsative wave signal is small. For this reason, it is difficult to obtain a stable measurement particularly for ICU patients during the anesthesia or after the operation.

When the cardiac output and blood volumes are measured by injecting the dye into blood, blood flow is impeded as the result of attaching the probe. This leads to deterioration of measurement accuracy and the reproducibility. In the clip setting applied to the ear lobe, the probe is easily moved when the subject moves. This results in instable measurement and great measurement errors.

SUMMARY OF THE INVENTION

Accordingly, an object of the present invention provide a method of measuring the quantity of attenuation of light when it passes through blood and a photo sensor used for the measurement, which realize a high precision pulsative wave spectral measurement while being free from blood flow impediment, body fluctuation, nervous reflection, and stimulation by nerve reflection, deep breathing, injection liquid, and the like.

To achieve the above object, there is provided a method of measuring the quantity of attenuation of light when it passes through blood in which a light emitting piece or a photo sensing piece is inserted into an external auditory canal of a living body and located near to an superficial temporal artery region, the photo sensing piece or the light emitting piece is set to a location near to the superficial temporal artery region on the temporofacial skin surface, and light that is emitted from the light emitting piece and transmitted through the superficial temporal artery region is received by the photo sensing piece.

According to aspect of the present invention, there is provided a photo sensor comprising: an external auditory canal arm having a light emitting piece or a photo sensing piece at the distal end, which is to be inserted into external auditory canal, contact means for bringing the distal end of the external auditory canal arm into contact with a location near to the superficial temporal artery region on the inner surface of the external auditory canal, and a mounting piece for setting the photo sensing piece or the light emitting piece to a location near to the superficial temporal artery region on the temporofacial skin surface.

In the photo sensor of the present invention, the light emitting piece and the photo sensing piece are attached to the distal ends of a pair of compressively holding means, respectively, one of the compressively holding means is the external auditory canal arm and the other thereof is a hold arm for holding the mounting piece.

In the photo sensor of the present invention, either of the external auditory canal arm and the hold arm of the compressively holding means includes a slip-out preventing means to be in contact with the skin.

In the photo sensor of the present invention, the slip-out preventing means is a means for compressively holding a helix of the ear, which is located at the end of the external auditory canal arm of the compressively holding means, which is opposed to the distal end thereof.

The photo sensor of the present invention further comprises stopper means for stopping the external auditory canal arm and the hold arm of the compressively holding means in a state that these arms are opened at a preset angle.

In the photo sensor of the present invention, the compressively holding means is attached to the holding means for compressively holding the head of the living body on both sides thereof.

In the light attenuation measuring method and the photo sensor of the present invention, the light emitting piece or the photo sensing piece inserted into the external auditory canal by the external auditory canal arm is brought into contact with the location near to the superficial temporal artery region in the external auditory canal through the contact means. The photo sensing piece or the light emitting piece is set to a location near to the superficial temporal artery region on the temporofacial skin surface by the mounting piece. Light that is emitted from the light emitting piece and transmitted through the superficial temporal artery region is received by the photo sensing piece. Accordingly, the superficial temporal artery is not pressed by the cartilage located near the external auditory canal, and a smooth blood flow is secured. Therefore, a variation of the quantity of light when passing through blood flowing through an artery of a living body, which is caused by light absorptive materials in the blood, can stably be detected, and oxygen saturation, cardiac output and blood volumes, and the like in the blood can be measured accurately.

In the photo sensor of the present invention, the compressively holding means consists of the external auditory canal arm and the hold arm. The photo sensing piece or light emitting is attached to the distal end of the external auditory canal arm, and set to the external auditory canal. The light emitting piece or the photo sensing piece is attached to the end of the hold arm is attached to a location near the ear on the outer surface of the temporal region. The superficial temporal artery region is compressively held by the compressively holding means. The measuring position is fixed. A variation of the quantity of light when passing through blood flowing through an artery of a living body, which is caused by light absorptive materials in the blood, can stably be detected, and oxygen saturation, cardiac output and blood volumes, and the like in the blood can be measured accurately.

In the photo sensor of the present invention, the compressively holding means includes the slip-out preventing means. Therefore, when the compressively holding means is attached to the external auditory canal and the temporal region, it can stably be held at fixed positions. When the body of the subject moves, the measuring instrument is not slipped out of the fixed positions. An accurate measurement is ensured.

In the photo sensor of the present invention, the slip-out preventing means compressively holds a helix of the ear, which is located at the end of the external auditory canal arm of the compressively holding means, which is opposed to the distal end thereof. The instrument can be fixed by the concha. The slip-out of it can be prevented further reliably, ensuring a stable measurement.

The photo sensor of the present invention further includes stopper means for stopping the external auditory canal arm and the-hold arm of the compressively holding means in a state that these arm are opened at a preset angle. Therefore, the compressively holding means can reliably be set at a preset position.

In the photo sensor of the present invention, the compressively holding means is compressively set to the head of the living body by the holding means. The measuring instrument can be set more easily and reliably.

BRIEF DESCRIPTION OF THE DRAWINGS

FIGS. 3 (a) and (b) are graphs comparatively showing the results of measuring pulsative wave signals by the photo sensor of the invention and the conventional one;

FIGS. 10 (a) (b) and (c) are explanatory diagrams showing another construction of a light emitting piece of the embodiment shown in FIG. 4 and a cross sectional view of state of mounting a photo sensor according to the second embodiment of the present invention;

DETAILED DESCRIPTION OF THE PREFERRED EMBODIMENTS

A method of measuring the quantity of attenuation of light when it passes through blood and a photo sensor need for the measurement will be described with reference to the accompanying drawings.

Figure 1:
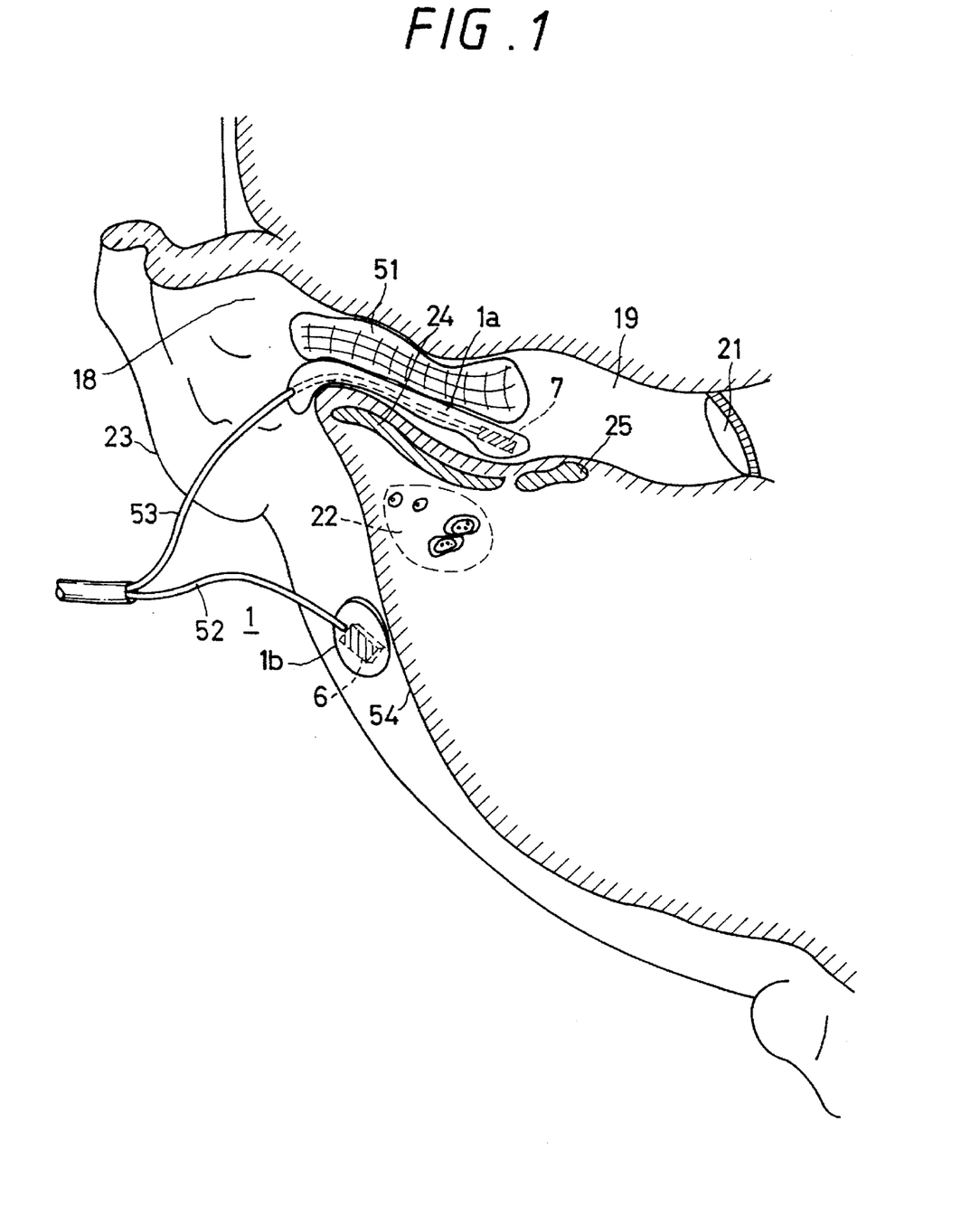
FIG. 1 is a cross sectional view taken on line X—X in FIG. 2 showing a state of mounting a photo sensor according to the first embodiment of the present invention.
Figure 2:
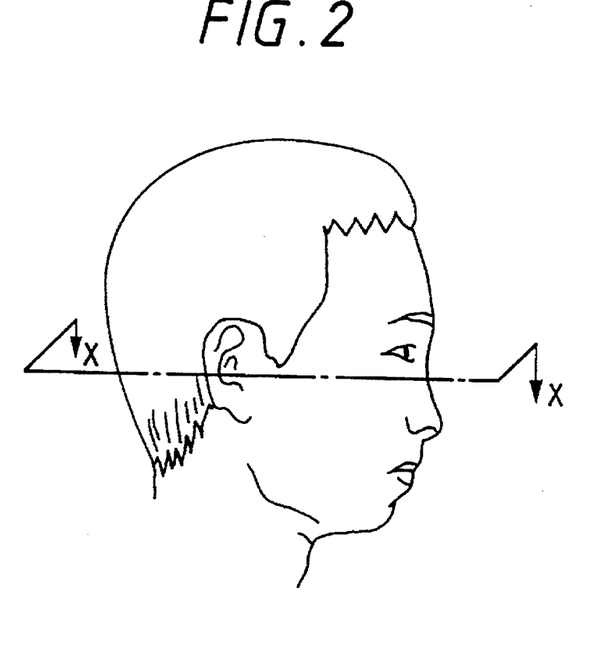
FIG. 2 is a side view showing measuring locations of a subject.

FIGS. 1 and 2 show a first embodiment of a photo sensor according to the present invention. FIG. 1 is a diagram showing a state that a photo sensor 1 is mounted on a head on line X—X in FIG. 2. The photo sensor 1 includes a substantially tubular, external auditory canal arm 1a, and a disc-like mounting piece 1b. A photo sensing piece 7, such as a photo diode, is attached to the distal end of the external auditory canal arm 1a. A light emitting piece 6, such as an LED, is attached to the central part of the mounting piece 1b in a state that the light emitting surface thereof is directed upward.

An elastic member 51 as a contact means is axially bonded to the photo sensing piece 7 of the external auditory canal arm 1a. More exactly, it is bonded to the surface of the photo sensing piece 7, which is reverse to the photo sensing surface thereof. The elastic member 51 is shaped like a column and made of porous material, such as expanded polyurethane. A bonding layer, not shown, is formed around the light emitting piece 6 on the surface of the mounting piece 1b. Lead wires 52 and 53 are connected to the light emitting piece 6 and the photo sensing piece 7, respectively. With the lead wires, a voltage is applied to the light emitting piece 6, to thereby activate the light emitting piece 6, and a signal produced from the photo sensing piece 7 when it receives light emitted from the light emitting piece, is received through the wire.

A method of measuring the quantity of light transmitted through blood by using the thus constructed photo sensor 1 will be described. As shown in FIG. 1, the distal end, which contains the photo sensing piece 7, of the external auditory canal arm 1a is inserted into the auditory meatus, through a cavum concha 18 of a temporal region of a subject, up to a location near to an external auditory canal 19. The photo sensing piece 7 of the external auditory canal arm 1a is put at a location near to a superficial temporal artery region 22. In this case, the light sensing face of the photo sensing piece 7 is directed toward the superficial temporal artery region In this state, the external auditory canal arm 1a is held at a location near to the external auditory canal 19, with the aid of the elasticity of the elastic member 51.

The mounting piece 1b with the light emitting piece 6 is attached to the surface of skin 54 by means of the adhesive layer. More exactly, the mounting piece 1b is attached to a location near to the superficial temporal artery region 22 on the skin surface of the temporal. In the measurement, light emitted from the light emitting piece 6 passes through the superficial temporal artery region 22 and reaches the photo sensing piece 7. A quantity of light, when passing through blood flowing through the superficial temporal artery, is varied by light absorptive materials in the blood. A variation of the quantity of the transmitted light is detected. Oxygen saturation, cardiac output and blood volumes, and the like in the blood are obtained on the basis of the detected variation of the quantity of the transmitted light.

In the present embodiment, an artery used for detecting a blood pulsative wave signal is the superficial temporal artery region 22 located between the light emitting piece 6 and the photo sensing piece 7. This portion, or the superficial temporal artery region 22, unlike an ear lobe 23, is little affected by a variation of ambient temperature, and exhibits temperature approximate to temperature of the body in a deep location. Accordingly, a circulation of blood is good and a pulsative wave signal of blood can stably be detected. It is noted that the photo sensing piece 7 is located within the external auditory canal 19. Therefore, it is little affected by external light rays and electrical disturbance. This fact also ensures a stable detection of a blood pulsative wave. Further, it is noted that the external auditory canal arm 1a is fixedly set in the external auditory canal 19 with the aid of the elastic member 51. This fact ensures that the external auditory canal arm 1a is stably set at a preset position, and that no external light reaches the photo sensing piece and little noise is generated. Additionally, it is noted that the elastic member 51 to be set in the external auditory canal 19 is made of porous material. The porous material allows an external sound to reach an ear drum 21.

A cartilaginous tragus 24 and a cartilaginous meatus 25 lie between the distal end of the external auditory canal arm 1a and the superficial temporal artery region 22. Therefore, when the external auditory canal arm 1a is set to a location near to the external auditory canal 19, it does not put any pressure on the superficial temporal artery region 22.

Figure 3A:
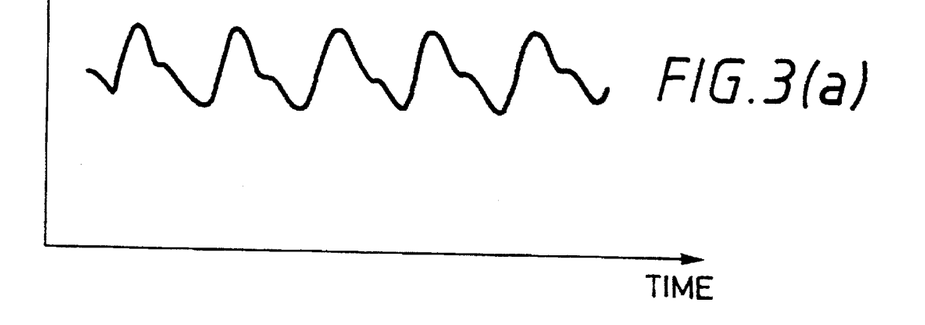
Figure 3B:
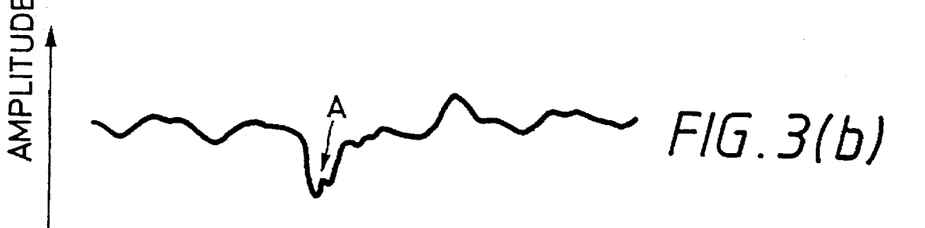

Waveforms of two pulse signals (a) and (b) are comparatively illustrated in FIGS. 3 (a) and (b). The pulse signal (a) was measured by the photo sensor 1 of the present embodiment shown in FIG. 1 operated in a state that the external auditory canal arm is inserted In the external auditory canal of a subject, and the mounting piece is attached to the skin surface of the temporal. The pulse signal (b) was measured by a conventional photo sensor operated in a state that it is attached to the ear lobe. As seen from FIGS. 3 (a) and (b), an amplitude of the pulse signal (a) produced by the photo sensor of the present embodiment is larger than that of the pulse signal (b) by the conventional photo sensor. When the subject flings his head, noise appears in the signal waveform (a) as indicated by an arrow A. However, in the signal waveform (b), no noise appears as shown.

Figure 4:
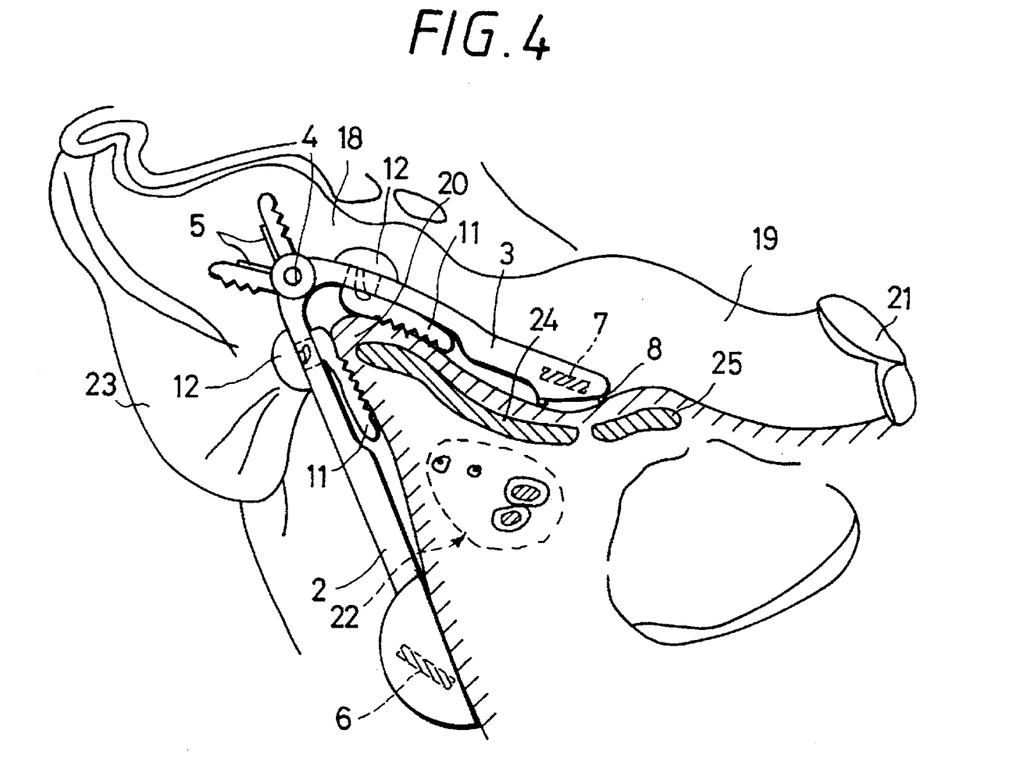
FIG. 4 is a cross sectional view showing a state of mounting a photo sensor according to the second embodiment of the present invention.
Figure 5:
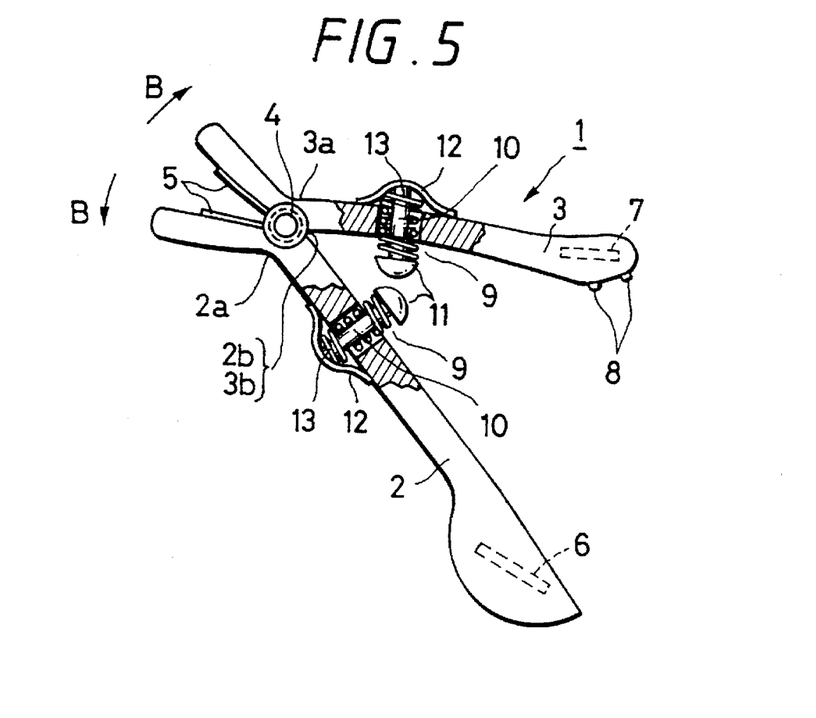
FIG. 5 is a side view, partly in cross section, showing the construction of the photo sensor of the second embodiment.

A second embodiment of the present invention will be described with reference to FIGS. 4 to 11. In FIG. 5, a photo sensor or probe 1 is provided with a pair of arms 2 and 3 as nipping means, viz., a hold arm 2 and an external auditory canal arm 3. These arms include bent portions 2a and 3a each located closer to one end thereof. The bent portions 2a and 3a have bearings 2b and 3b. A shaft 4 is passed through the paired bearings 2b and 3b. The arms 2 and 3, coupled with each other, are rotatable about the shaft 4. A coiled spring 5 is wound around the shaft 4. Both ends of the coiled spring 5 are put on the inner surfaces of the shorter sides of the arms 2 and 3. The coiled spring 5 thus assembled urges the arms 2 and 3 so as to open the shorter sides thereof as indicated by arrows B.

A light emitting piece 6, such as an LED and a photo sensing piece 7, such as a PD, are attached to the distal ends of the long sides of the arms 2 and 3 in a state that the photo sensing face of the light emitting piece 6 is opposed to the light emitting face of the photo sensing piece 7. The hold arm 2 with the light emitting piece 6 is usually selected to be longer than the external auditory canal arm 3 with the photo sensing piece 7, in connection with a location of the body where the photo sensor 1 is to be set, which will be described later. Protrusions 8 are formed on the photo sensing face of the external auditory canal arm 3. With provision of the protrusions, blood flow is little impeded at the pressed parts. Further, the photo sensing face of the photo sensing piece 7 is covered with a transparent resin, so that cerumen, if it is stuck thereto, can easily be removed.

If required, the transparent resin covering the photo sensing face of the photo sensing piece 7 may be shaped to fit to the shape of the inner wall of the external auditory canal 19, without forming the protrusions. In this case, some impediment of blood flow is inevitable. If the resin cover is so shaped, the photo sensor 1 may be applied to the ear more safely, viz., without inflicting any wound on the inner wall of the external auditory canal 19. Further, the external auditory canal arm 3 may be brought into close contact with the inner wall of the external auditory canal 19. Accordingly, a stable measurement is ensured.

The arms 2 and 3 are provided with pressure mechanisms 9 as slip-out preventing means. Each of the pressure mechanisms 9 includes a shaft 10, a pushing piece 11, a stopper 12, and a coiled spring 13. In the pressure mechanism, the shaft 10 is movable in the direction orthogonal to the axial direction of the arm 2 or 3. The pushing piece 11 is fastened to the end of the shaft 10 protruded inward from the arm 2 or 3. The stopper 12 is located in opposition to the other end of the shaft 10 protruded outward from the arm 2 or 3. The coiled spring 13 is applied to the shaft 10 between the pushing piece 11 and the stopper 12. The coiled springs 13 urge the pushing pieces 11 of the arms 2 and 3 of the photo sensor 1 so as to approach to each other. A protrusion for prevention the shaft 10 from being slipped off is formed at the end of the shaft 10, which faces the stopper 12.

Figure 6:
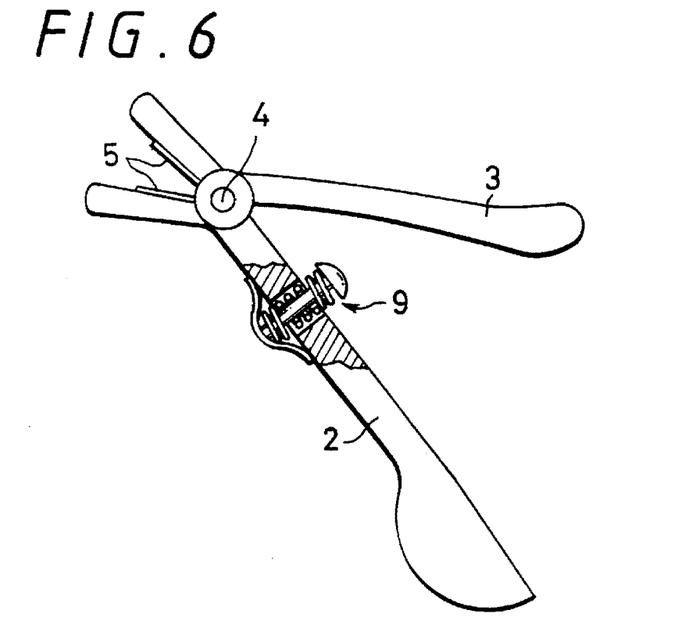
FIG. 6 is a side view, partly in cross section, showing a first modification of the photo sensor of FIG. 5.
Figure 7:
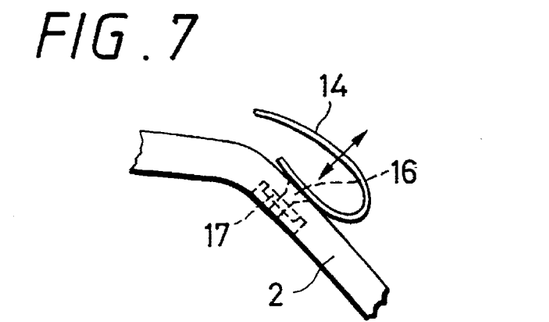
FIG. 7 is a side view, partly in cross section, showing a second modification of the photo sensor of FIG. 5.
Figure 8:
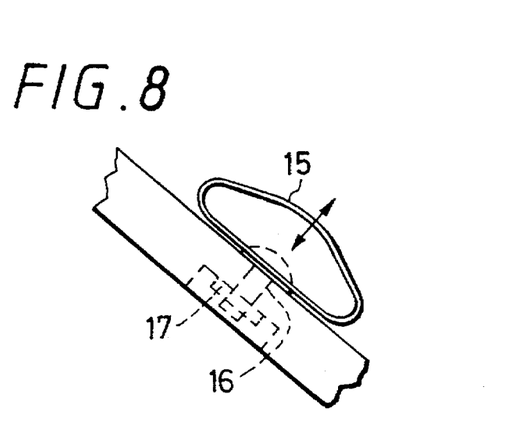
FIG. 8 is a side view, partly in cross section, showing a third modification of the photo sensor of FIG. 5.

The arms 2 and 3 may be respectively provided with the pressure mechanisms 9 as shown in FIG. 5 or either of them, for example, the hold arm 2 alone, may be provided with the pressure mechanism 9 as shown in FIG. 6. Each pushing piece 11 may be spherical in shape as shown in FIG. 5. It may also be a plate spring 14 shaped like U in cross section as shown in FIG. 7 or a plate spring 15 shaped like a ring in cross section as shown in FIG. 8. In the case of the plate spring 14 or 15, it is fastened to the hold arm 2 by means of the combination of a screw 16 and a nut 17, as shown in FIGS. 7 or 8. Further, the pushing piece 11 may be shaped like a flat plate as shown in FIG. 4. In this case, a contact area thereof is increased.

The mounting of the photo sensor 1 having the pushing pieces 11 each shaped like a flat plate on the body of a living body or a subject will be described with reference to FIG. 4. The end part, which contains the photo sensing piece, of the external auditory canal arm 3 of the photo censor 1 is inserted into the external auditory canal, through a cavum concha 18 of a temporal region of a subject, up to a location near to an external auditory canal 19. The hold arm 2 having the light emitting piece is placed on a mid location between the temple and the ear lobe 20. In this state, the coiled spring 5 urges the end parts, which contain the light emitting piece and the photo sensing piece, of the arms 2 and 3 to respectively be pressed against the temporal region and the inner wall of the location near the external auditory canal 19. In FIG. 4, reference numeral 21 designates an ear drum.

The location near the external auditory canal 19 is slanted with respect to the outer surface of the temporal region at an acute angle. Accordingly, when the arms 2 and 3 are set to these portions of the ear of the subject, these tend to slip out of the slanted portions. To cope with this, the pushing pieces 11 of the pressure mechanisms 9 mounted on the arms 2 and 3 are respectively brought into contact with the inner surface of the entrance of the external auditory canal 19 and the outer surface of the ear lobe 20, and held thereat by the urging forces of the coiled springs 13 associated therewith. It is noted that the protrusions 8 are provided near the photo sensing piece 7 of the external auditory canal arm 3. When the external auditory canal arm 3 is pressed against the inner surface of the location near the external auditory canal 19, the blood flow would be impeded under the inner surface or the inner surface would get hurt unless the protrusions 8 are used.

In the present embodiment, an artery used for detecting a blood pulsative wave signal is the superficial temporal artery 2 located between the light emitting piece 6 and the photo sensing piece 7. This portion, or the superficial temporal artery region 22, unlike an ear lobe 23, is little affected by a variation of ambient temperature, and exhibits temperature approximate to temperature of the body in a deep location. Accordingly, a circulation of blood is good and a pulsative wave signal of blood can stably be detected. It is noted that the photo sensing piece 7 is located within the external auditory canal 19. Therefore, it is little affected by external light rays. This fact also ensures a stable detection of a blood pulsative wave. Further, it is noted that the arms 2 and 3 are set at preset locations by the coiled spring 5, and are prevented from being slipped out of the preset locations by the pressure mechanisms 9. Thus, no slip-out or dislocation of the probe 1 takes place.

A cartilaginous tragus 24 and a cartilaginous meatus 25 lie between the distal end of the external auditory canal arm 3 and the superficial temporal artery region 22. Therefore, when the arms 2 and 3 are set to preset locations, the arms do not put any pressure on the superficial temporal artery region 22. It is noted that the pressure mechanisms 9 are set to locations apart from the superficial temporal artery region 22. Accordingly, if those are forcibly pressed against the locations, the blood flow measurement is little affected by the forcible pressing actions thereof. Where the pressures by the arms 2 and 3 are reduced, there is a less chance that the surface or skin near to the external auditory canal 19 gets hurt. The photo sensing piece 7 of the distal end of the external auditory canal arm 3 may be covered with soft material, such as sponge. In this case, after the sponge cover is used, it is thrown away. By so doing, the probe can be used with the feeling of soft touch.

Figure 9:
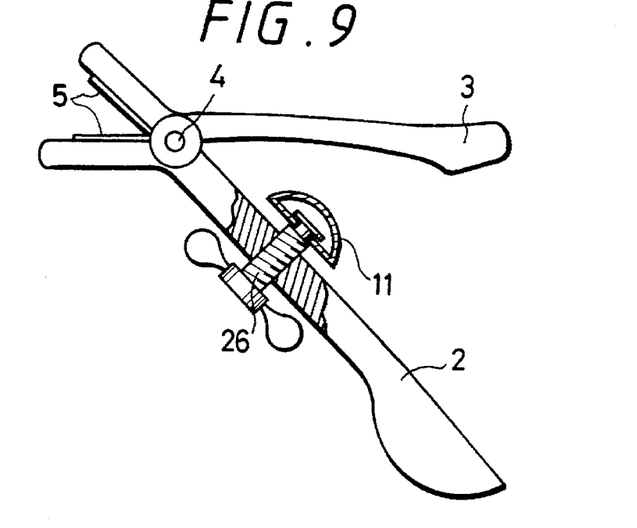
FIG. 9 is a side view, partly in cross section, showing a fourth modification of the photo sensor of FIG. 5.

In the present embodiment, each of the pressure mechanisms 9 is urged by the coiled spring 13 or the plate spring 14 or 15. However, it may be fixed by a screw as shown in FIG. 9. As shown in FIG. 9, a thumbscrew 26 is screwed into the hold arm 2 at a right angle, and a pushing piece 11 is fixed to the tip top of the thumbscrew 26. With turn of the thumbscrew 26, the pushing piece 11 advances and retards. If a nut, not shown, is set to the shaft part of the thumbscrew 26, the pushing piece 11 may be set to a preset position.

Figure 10A:
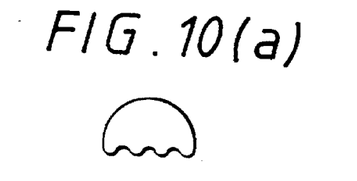
Figure 10B:
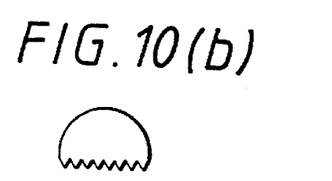
Figure 10C:
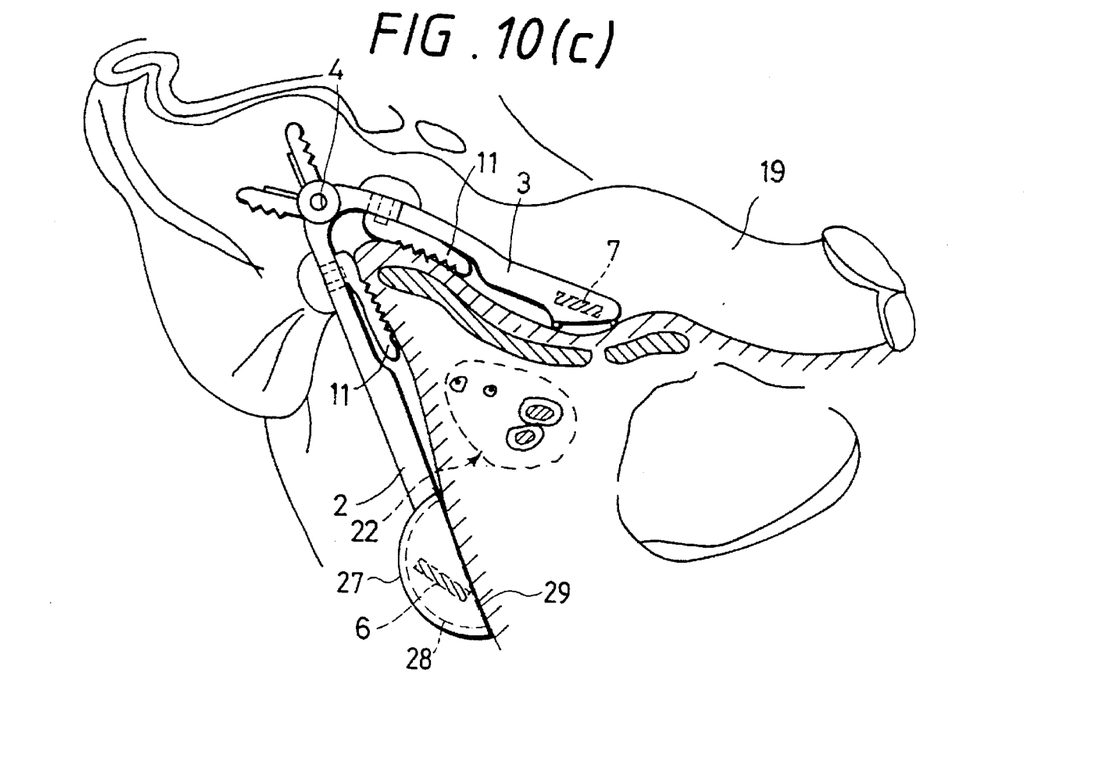
Figure 11:
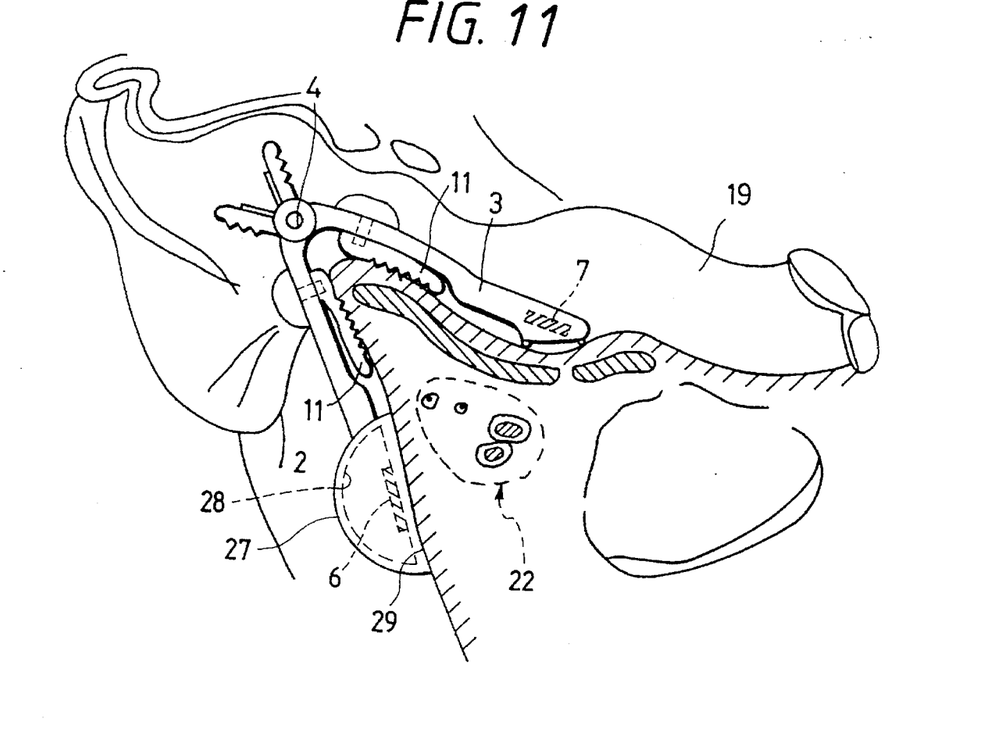
FIG. 11 is an explanatory diagram showing another arrangement of the light emitting piece and the photo sensing piece shown in FIG. 10.

In examples shown in FIGS. 10 and 11, a cover member 27, which covers the light emitting piece 6, is spherical in shape. A reflecting plate 28 is provided on the inner surface of the spherical cover member 27. A scattering plate 29 is mounted on the light emitting surface. With this construction, light, which is emitted from the light emitting piece 6, efficiently travels toward the light emitting surface, and is scattered by the scattering plate 29. A broader area of the superficial temporal artery region 22 is illuminated with the scattered light. To secure a more reliable attachment of the hold arm 2 to the temporal region, the surface of the scattering plate 29 may be shaped wavy in cross section as shown in FIG. 10(a) or like a saw-tooth in cross section as shown in FIG. 10(b). To attach the light emitting face of the light emitting piece to the temporal region, a double-coated tape or adhesive foam may be stuck to the peripheral area of the light emitting surface.

The hold arm 2 with the light emitting piece 6 is longer than the external auditory canal arm 3 with the photo sensing piece 7. Distance between the light emitting piece 6 and the photo sensing piece 7 is longer than that when the arms 2 and 3 are equal in length. If the distance is so selected, the superficial temporal artery region 22 located in a relatively large depth when viewed in the external auditory canal 19 can more widely be illuminated with light. Accordingly, a larger quantity of information on blood flowing through the artery can be gathered, and a stable pulsative wave spectral measurement is realized. The light emitting piece 6 may be slanted to the surface of the temporal region, but oriented in parallel with the photo sensing piece 7, as shown in FIGS. 10 (a) and (b). Alternatively, the light emitting piece 6 may be oriented in parallel with the surface of the temporal region, but slanted to the photo sensing piece 7, as shown in FIG. 11.

The construction of a third embodiment of the present invention is shown in FIGS. 12 to 18. In these figure, like or equivalent potions are designated by like reference numerals in FIGS. 4 and 5 showing the second embodiment. In the present embodiment, the slip-out preventing means consists of a pair of pressure levers 30. The pressure levers 30 are rotatably supported at the mid points by a shaft 4, which also supports the arms 2 and 3. Stopper means for the pressure levers 30 are provided with respect to the shaft 4.

Figure 12:
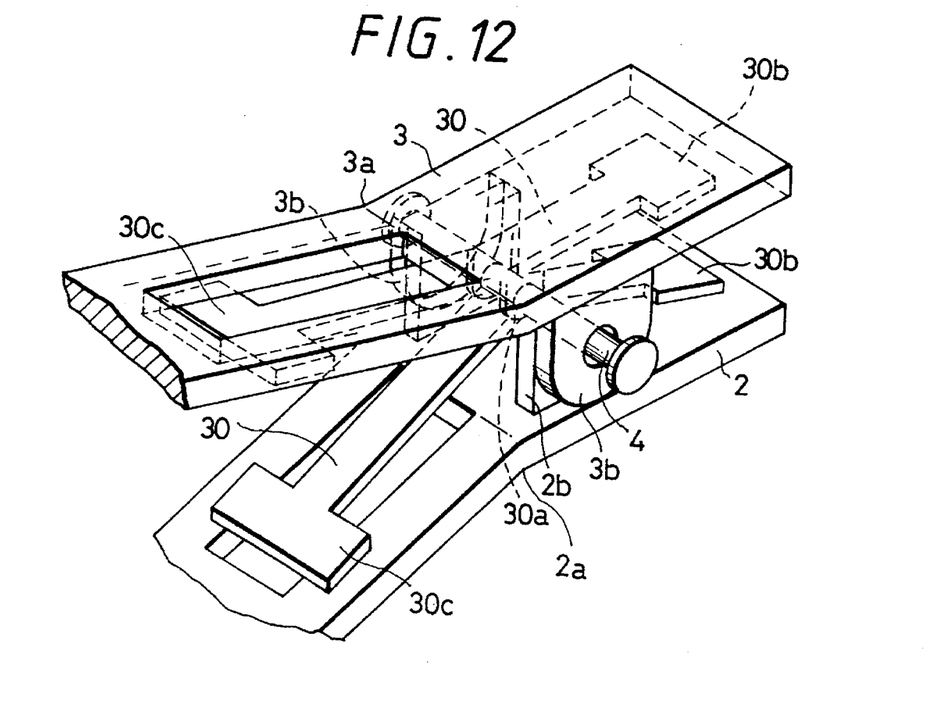
FIG. 12 is a perspective view showing the construction of a third embodiment of a photo sensor according to the present invention.
Figure 13:
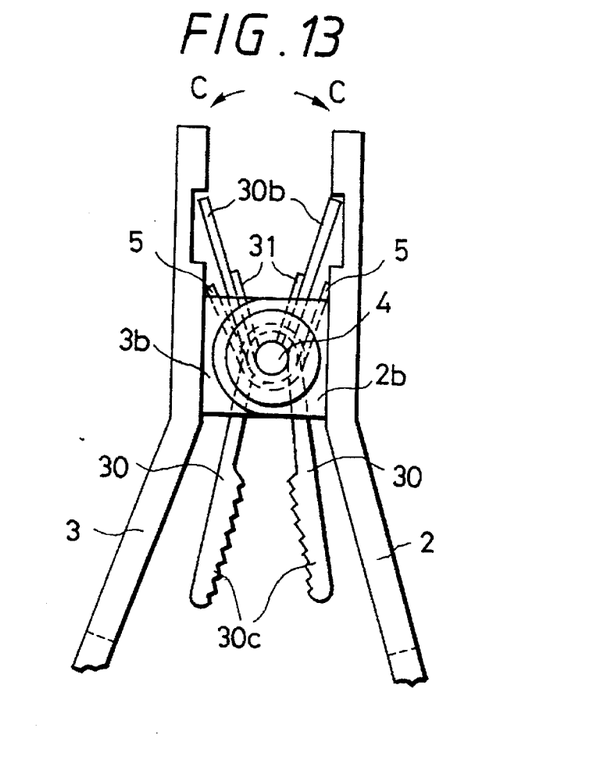
FIG. 13 is a side view showing the photo sensor of FIG. 12.
Figure 14:
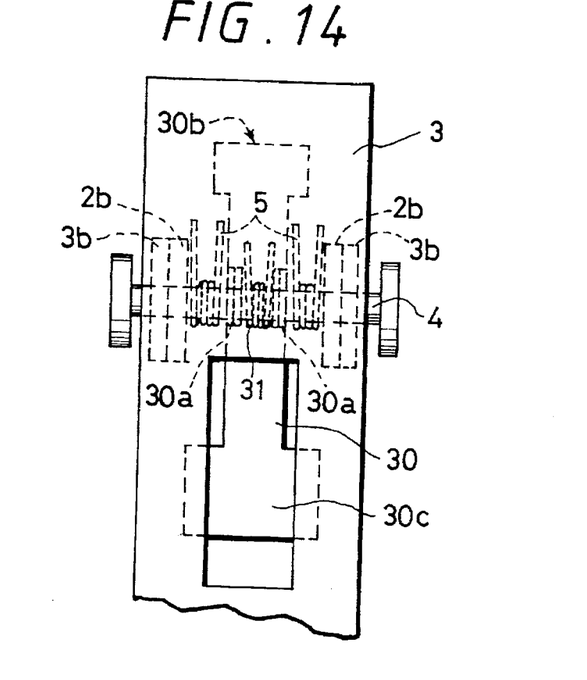
FIG. 14 is a a plan view showing the photo sensor of FIG. 12.

Bearings 3b are provided at both ends of a bent portion 3a of the external auditory canal arm 3, while being oriented at a right angle to the arm 3. Bearings 2b are provided at the locations near both ends of a bent portion 2a of the hold arm 2 while being oriented at a right angle to the hold arm 2. As in the second embodiment, the shaft 4 is inserted into the bearings 2b and 3b. The arms 2 and 3 are rotatably supported on the shaft 4 by the bearings 2a and 3b. A light emitting piece 6 and a photo sensing piece 7 are respectively attached to the distal ends of the arms 2 and 3 as in the second embodiment shown in FIGS. 4 and 5.

A pair of coiled springs 5 are put around the shaft 4 between the pair of the bearings 2b. Both ends of the coiled springs 5 are put on the inner surfaces of the shorter sides of the arms 2 and 3. The coiled springs 5 urge the shorter sides of the 2 and 3 to open as indicated by arrows C.

Figure 15:
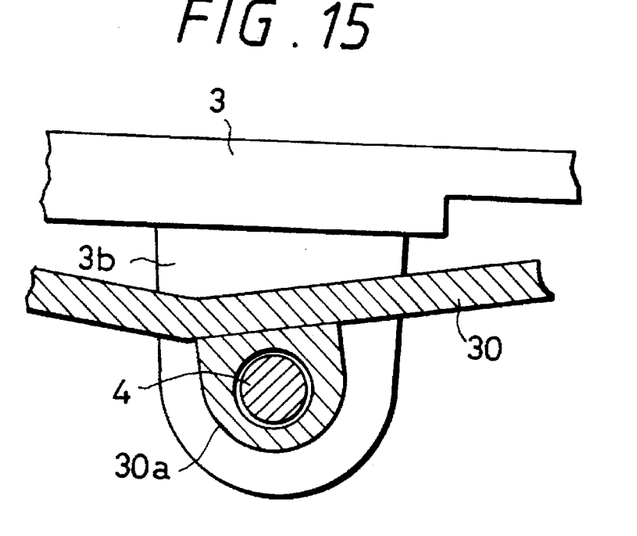
FIG. 15 is an enlarged side view showing the bearing shown in FIG. 12.

A pair of pressure lever 30 as slip-out preventing means are rotatably supported by the shaft 4 between the coiled springs 5. The pressure levers 30 are disposed substantially parallel to the inner sides of the arms 2 and 3. A pair of bearings 30a are disposed at the mid points thereof at a right angle to the surfaces of the pressure levers 30. The bearings 30a are rotatably supported by the shaft 4 as shown in FIG. 15. The first ends 30b of the pressure levers 30 are in contact with the inner surfaces of the shorter sides of the arms 2 and 3. The second ends of the pressure levers 30 are expanded in width to form pressure portions 30c.

A coiled spring 31 is put around the shaft 4 between the paired bearings 30a. The ends of the coiled spring 31 are put on the inner surfaces of the sides of the pressure levers 30, which are opposite to the sides thereof including the pressure means 30c. The coiled spring 31 thus arranged urges the sides of the pressure levers 30 on which the coiled spring 31 are put, to open as indicated by arrows C in FIG. 13.

Figure 16:
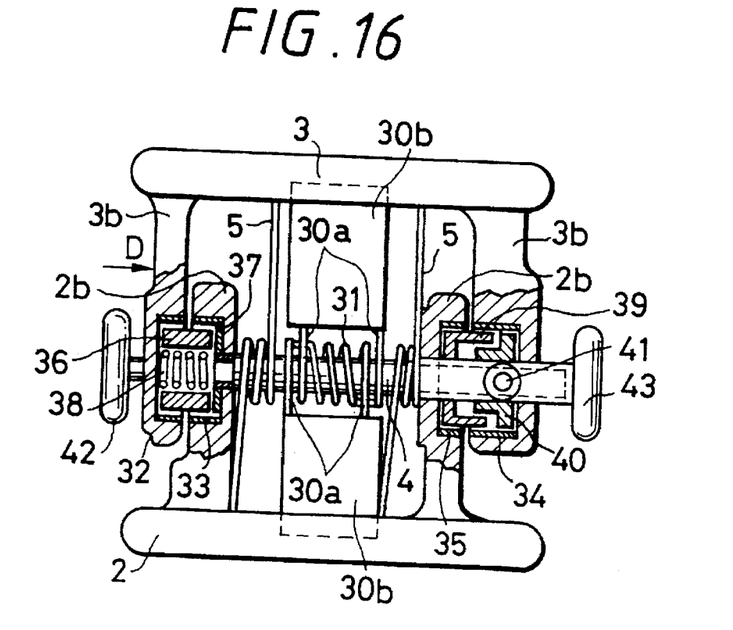
FIG. 16 is a side view, partly in cross section, showing the structure shown in FIG. 12 when arm stopper means are used.

Stopper means for stopping the paired arms 2 and 3 in a state that the arms 2 and 3 are opened at a preset angle with respect to the shaft 4, will be described with reference to FIGS. 16 to 20. In FIG. 16, ring-like fixing members 32, 33, 34 and 35 are fit and fixed to the pairs of right and left bearings 2b and 3b of the arms 2 and 3. The fixing members 32 to 35 are made of hard synthetic material. The inner surfaces of the ring-like fixing members include saw-tooth stopper parts.

A ring-like, first pressure member 36 made of rubber containing metal fibers is coaxially placed within the fixing members 32 and 33 fastened to the right bearings 2b and 3b of those right and left bearing pairs. One end of the first pressure member 36 is in contact with the inner face of the bearing 3b, while the other end of the first pressure member 36 is in contact with a collar 37, which is fastened to one end of the shaft 4 in a coaxial fashion. The shaft 4 passes through the bearing 2b, and the collar 37 is disposed within the bearing 2b. A coiled spring 38 is inserted between the collar 37 and the inner end face of the bearing 3b, to thereby urge the collar 37 in the direction of an arrow D.

A second pressure member 39, which is made of rubber containing metal fibers and shaped like a tube with the bottom, is coaxially placed within the fixing members 34 and 35 fastened to the left bearings 2b and 3b of those right and left bearing pairs. One end of the second pressure member 39 is in contact with the outer face of the bearing 3b, while the other end of the second pressure member 39 is in contact with a collar 40, which is fastened to one end of the shaft 4 in a coaxial fashion. The shaft 4 passes through the bearing 2b, and the collar 40 is disposed within the bearing 3b. A through-hole 39a through which the shaft 4 is to be inserted is formed at the central part of the bottom of the second pressure member 39.

Figure 17:
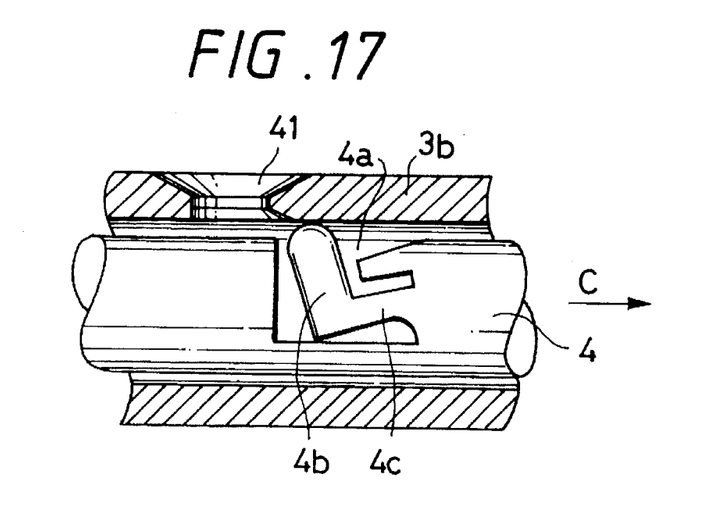
FIG. 17 is an enlarged, side view showing a key portion of the shaft of FIG. 16.
Figure 18:
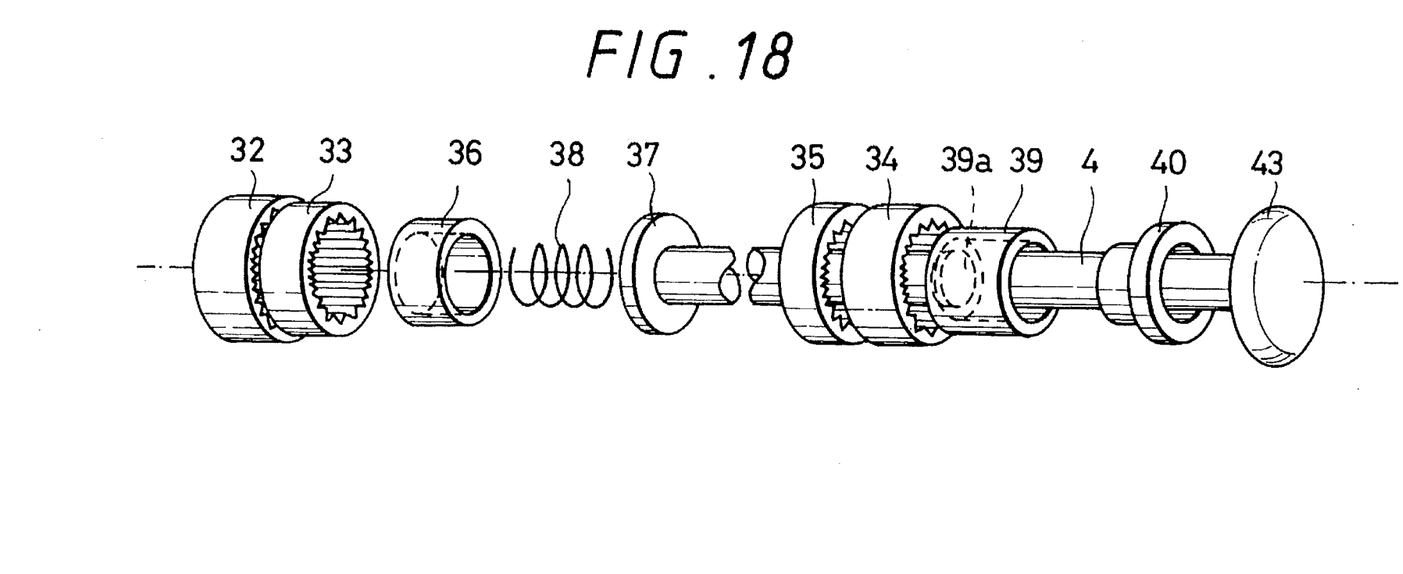
FIG. 18 is an exploded view showing the construction of the stopper means of FIG. 16.

A round hole 41 is formed in the circumferential wall of the bearing 3b, while reaching the center hole thereof. A cutout 4a is formed in the outer surface region of the shaft 4 as shown in FIG. 17. Within the cutout 4a, a protruded part 4b is protruded from the shaft 4. The protruded part 4b is brought into contact with the inner surface of the bearing 3b or put into the round hole 41. In this case, a base 4c of the protruded part 4b is elastically deformed. Buttons 42 and 43 are mounted on both ends of the shaft 4, which are located outside the right and left bearings 3b. In the present embodiment, the shaft 4 having the buttons 42 and 43 at both ends is separated into two, right and left sides, at the collar 37.

Figure 19:
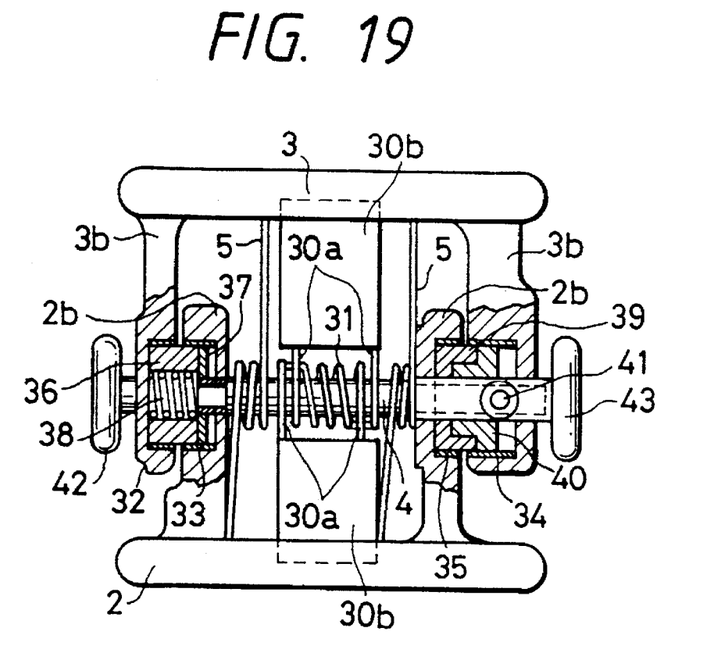
FIG. 19 is a front view, partly in cross section, showing a state that the arm shown in FIG. 16 are stopped.
Figure 20:
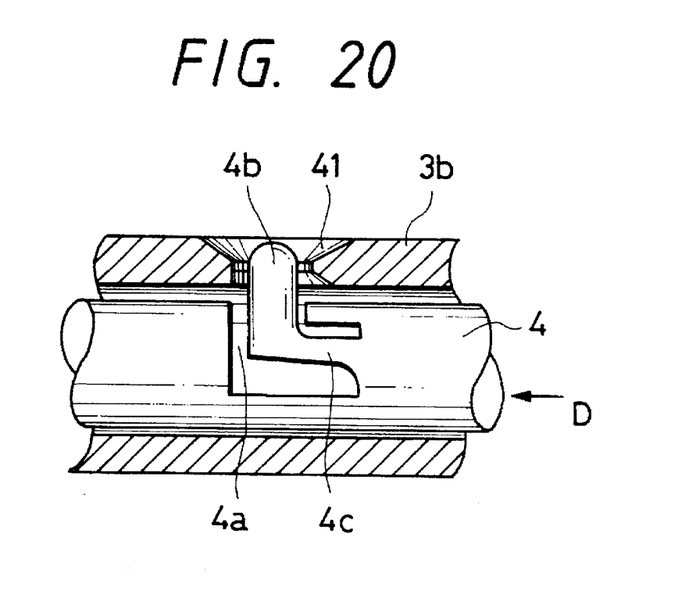
FIG. 20 is an enlarged, cross sectional view showing a state of the shaft when the arm of FIG. 16 is stopped.

The operation of the second embodiment thus constructed will be described. FIGS. 16 and 17 illustrate the structure of the probe according to the third embodiment of the present invention in a state that the arms 2 and 3 are rotatable with respect to the shaft 4. FIGS. 19 and 20 illustrate the structure of the same probe in a state that the arms 2 and 3 are locked or unrotative with respect to the shaft 4. When the shaft 4 is moved in the direction of an arrow E, the tip top of the protruded part 4b comes in contact with the inner surface of the bearing 3b, and the shaft 4 is movable In the axial direction, as shown in FIG. 17. In this state, as shown in FIG. 16, the collars 37 and 40 do not push the first and second pressure members 36 and 39. When the shaft 4 is moved in the direction of an arrow F, the protruded part 4b input into the round hole 41 of the bearing 3b as shown in FIG. 20. In this state, the shaft 4 is immovable in the axial direction. In this state, the collars 37 and 40 push and compress the first and second pressure members 36 and 39. As a result, the first and second pressure members 36 and 39 are radially expanded, the outer surfaces thereof come in contact with the inner surfaces of the fixing members 32 to 35. In this state, the bearings 2b and 3b are immovable with respect to the shaft 4. In other words, the arms 2 and 3 are fixed with respect to the shaft 4. Accordingly, the arms 2 and 3 are reliably attached to the temporal region and the external auditory canal of the subject, ensuring a stable pulsative wave spectral measurement.

To remove the probe 1 from the head, an operator inserts his finger or a ball-point pen, for example, into the round hole 41 to push the protruded part 4b, to thereby disengage the protruded part 4b from the round hole 41. Then, the state shown in FIG. 17 is set up. The first and second pressure members 36 and 39 are released from being pushed and compressed, as shown in FIG. 16. In this state, the arms 2 and 3 are rotatable with respect to the shaft 4.

In the present embodiment, the arms 2 and 3 may be fixed to the shaft 4 through the first and second pressure members 36 and 39. As a result, the distance between the light emitting piece 6 and the photo sensing piece 7 is fixed, thereby realizing a high precision pulsative wave spectral measurement.

Figure 21:
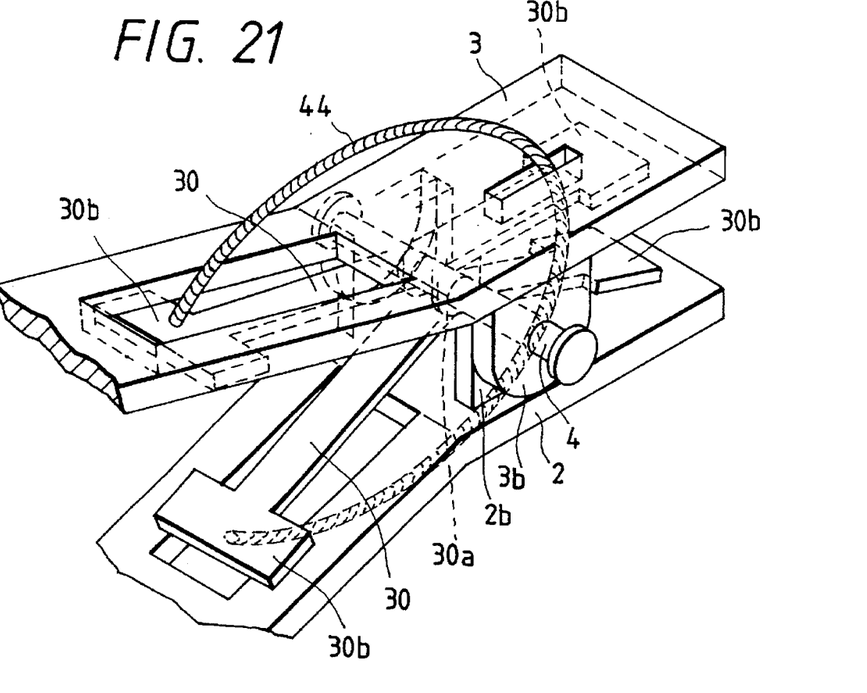
FIG. 21 is a perspective view showing the construction of a modification of the second embodiment shown in FIG. 21.
Figure 22:
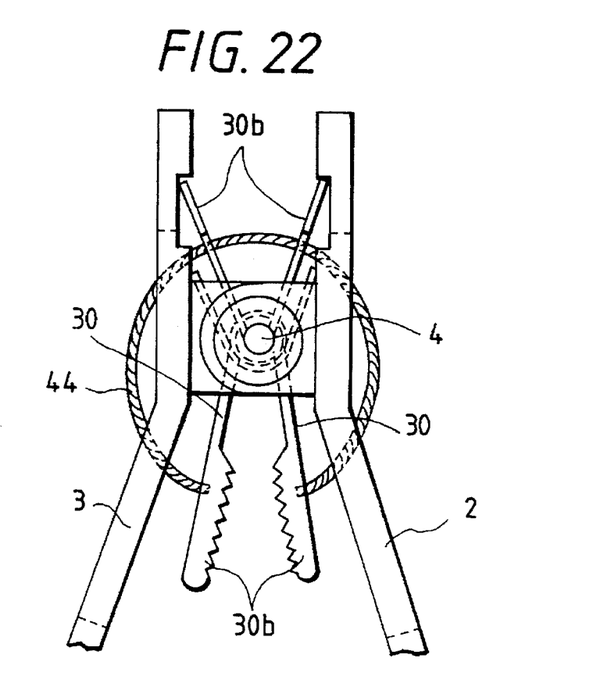
FIG. 22 is a side view showing the construction of FIG. 21.
Figure 23:
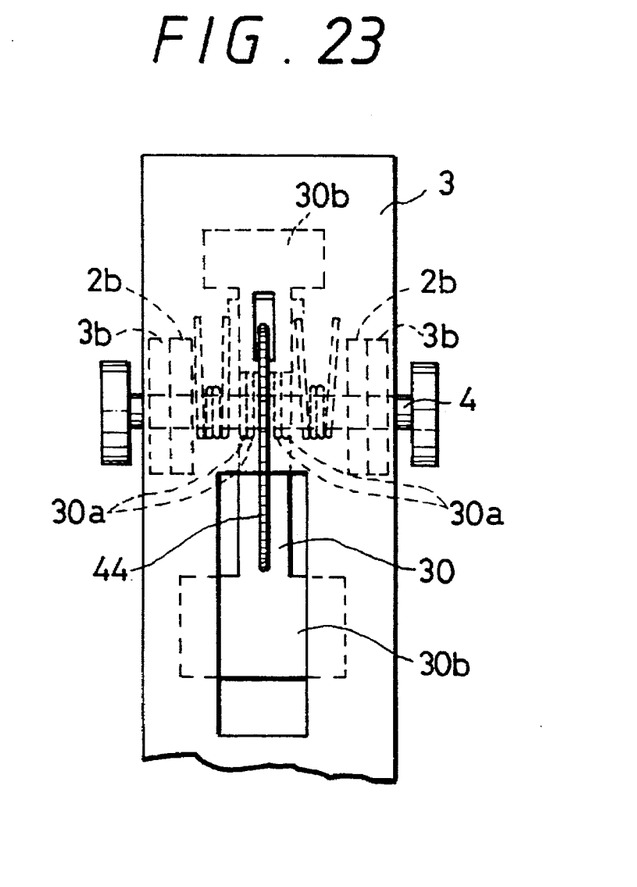
FIG. 23 is a plan view showing the construction of FIG. 21.

In the third embodiment, the coiled spring 31 is used as the means for urging the pressure portions 30b of the pressure levers 30. A U-shaped plate spring 44 as shown in FIGS. 21 to 23 may be used in place of the coiled spring. The plate spring 44 is held by the arms 2 and 3 in a state that both ends of the U-shaped plate spring 44 are in contact with the outside of the pressure portions 30b of the pressure levers 30.

Figure 24:
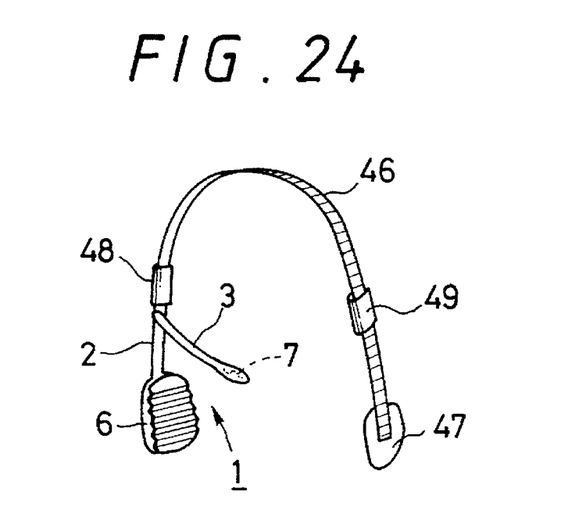
FIG. 24 is a perspective view showing the construction of an example of a band for supporting a photo sensor of the present invention.
Figure 25:
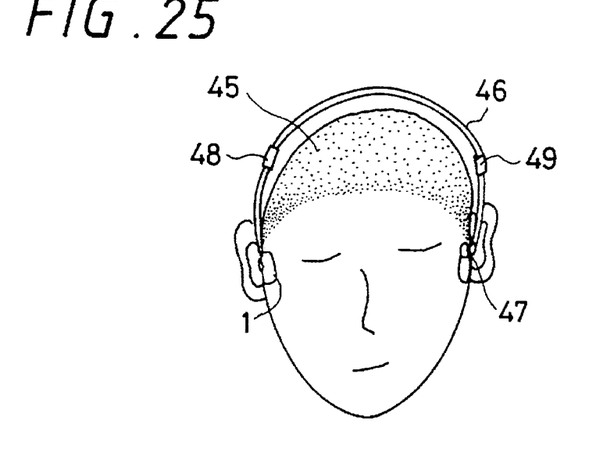
FIG. 25 is a front vies showing a state that the band shown in FIG. 24 is set to the head of a subject.

To set the probe 1 to the head 45, the probe 1 is mounted on the first end of an inverted-U shaped band 46 as shown in FIG. 24, and the arm 3 with the photo sensing piece 7 is inserted into the external auditory canal as shown in FIG. 25.

The hold arm 2 with the light emitting piece 6 and the second end 47 of the band 46 are respectively set to the right and left bases of the bone of the head 45. Reference numerals 48 and 49 indicate length adjustors for adjusting the length of the band 46.

Figure 26:
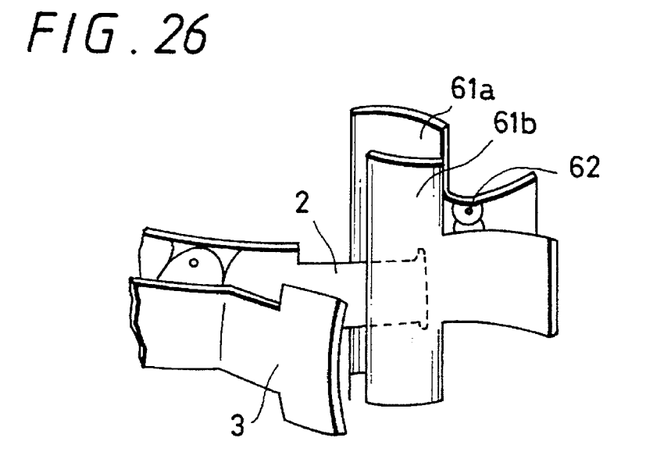
FIG. 26 is a perspective view showing the construction of a clip used for fixing the photo sensor shown in FIG. 4.
Figure 27:
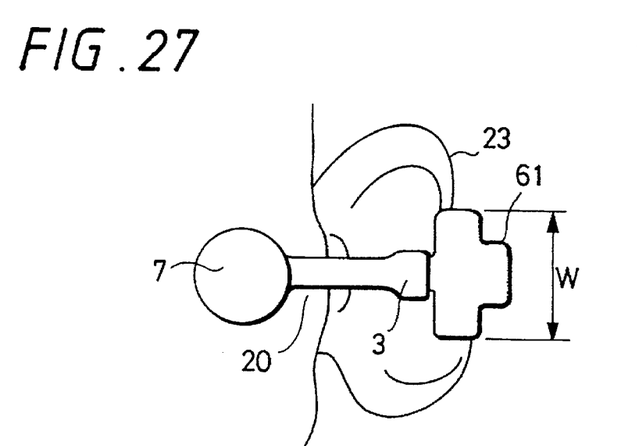
FIG. 27 is a front view showing a state that the photo sensor is set to the ear lobe by the clip of FIG. 26.

A clip 61 may be used to fix the shorter side of each of the arms 2 and 3 to the ear lobe 23, as shown in FIGS. 26 and 27. In this case, the pressure mechanisms 9 are omitted. The clip 61 is constructed such that a pair of holder pieces 61a and 61b are coupled together at the mid points so as to be turned about a shaft 62. The end faces of the holder pieces 61a and 61b where the holder pieces come in contact with the ear lobe 23, are broad in width W. With this, the probe 1 may stably be fixed to the ear lobe 23.

In the present embodiment, the probe 1 may be fixedly set to the head of a subject in a simple manner. When it is set, a stable measurement can be done even he moves. Particularly, the probe 1 of the present embodiment effectively operates particularly for small and soft ear lobes 23. One end of either of the arms 2 and 3 may be bonded to the wider side of the clip 61.

It should be understood that the present invention may variously be modified, changed and altered within the scope of the present invention. For example, the photo sensing piece 7 may be attached to the outside of the temporal region, while the light emitting piece 6, to a location near to the external auditory canal.

In a method of measuring the quantity of attenuation of light when it passes through blood and a photo sensor used for the measurement, which are constructed according to the present invention, a light emitting piece and a photo sensing piece are attached to the ends of a pair of arms, respectively. The light emitting piece or the photo sensing piece is mounted on a location near an ear on the outer surface of the temporal region of the head of a subject, while the photo sensing piece or the light emitting piece is inserted into the auditory meatus up to a location near to the external auditory canal. A variation of the quantity of light when passing through blood flowing through the superficial temporal artery, which is caused by light absorptive materials in the blood, is detected. The light absorptive materials can be detected at a location near to the external auditory canal where the average temperature, approximate to temperature in a deep part of the body, is higher than that on the ear lobe or the concha exposed to air. A detected pulsative wave signal is sharp in waveform and large in amplitude. The measurement is not affected by blood flow impediment, body fluctuation, nervous reflection, and the like. Accordingly, a high precision pulsative wave spectral measurement is realized. Oxygen saturation, cardiac output and blood volumes, and the like in the blood can accurately be measured. The compressively holding means provided with the slip-out preventing means. The photo sensor can stably be held at preset positions on the body of a subject while being free from the slip-out of the sensor. An accurate spectral measurement of pulsative wave signals is secured.

What is claimed is:

1. A photo sensor comprising:
    an external auditory canal arm having one of a light emitting element and a photo sensing element at a distal end for insertion into an external auditory canal;
    a contact member for bringing the distal end of the external auditory canal arm into contact with a location near to a superficial temporal artery region on an inner surface of the external auditory canal; and
    a contact member for setting one of said light emitting element and said photo sensing element, other than that which is at said distal end, to a location near to the superficial temporal artery region on the temporofacial skin surface and below the earlobe.

2. A photo sensor according to claim 1, further comprising:
    a pair of compressively holding arms, one of which corresponds to the external auditory canal arm and having said distal end, and the other of which being a holding arm for holding the contact member.

3. A photo sensor according to claim 2, wherein a slip-out preventing member to be in contact with the skin is provided with at least one of the external auditory canal arm and the holding arm.

4. A photo sensor according to claim 3, wherein the slip-out preventing member is for compressively clamping a helix of the ear and is located at the end of the holding arm, opposite to the distal end of an external auditory canal arm.

5. The photo sensor according to claim 3 or 4, further comprising:
    a stopper member for stopping the external auditory canal arm and the holding arm at a predatemined angle defined therebetween.

6. The photo sensor according to claim 2, in which the compressively holding arms are attached to the holding member for compressively holding the head of a living body on both sides thereof.

7. The photo sensor according to claim 1, wherein the light emitting element transmits light through the superficial temporal artery to the photo sensing element.

8. A method of measuring the quantity of attenuation of light when it passes through blood comprising the steps of:
    inserting a light emitting element of a photo sensing element into an external auditory canal of a living body and locating the element near a superficial temporal artery region;
    setting the ocher of the photo sensing element or the light emitting element to a location near to the same superficial temporal artery region on the temporofacial skin surface; and
    detecting a light emitted from the light emitting element and transmitted through the same superficial temporal artery region by the photo sensing element.

9. A method as claimed in claim 8, wherein said location is below the earlobe.

10. A photo sensor comprising:
    an external auditory canal arm having one of a light emitting element and a photo sensing element at a distal end for insertion into an external auditory canal;
    a contact member for bringing the distal end of the external auditory canal arm into contact with a location near to a superficial temporal artery region on an inner surface of the external auditory canal;
    a contact member for setting one of said light emitting element and said photo sensing element, other than that which is at said distal end, to a location near to the superficial temporal artery region on the temporofacial skin surface;
    a pair of compressively holding arms, one of which corresponding to the external auditory canal arm and having said distal end, and the other of which being a holding arm for holding the contact member; and
    a stopper member for stopping the external auditory canal arm and the holding arm at a predetermined angle defined therebetween.

* * * * *